United States Patent [19]

Ware, Jr. et al.

[11] 3,931,202

[45] Jan. 6, 1976

[54] PYRIDYL PHENYL-CARBAMATE RODENTICIDES

[75] Inventors: J. Edgar Ware, Jr., Quakertown; Edward E. Kilbourn; David L. Peardon, both of Chalfont, all of Pa.

[73] Assignee: Rohm and Haas Company, Philadelphia, Pa.

[22] Filed: June 12, 1974

[21] Appl. No.: 478,678

Related U.S. Application Data

[63] Continuation-in-part of Ser. Nos. 428,463, Dec. 26, 1973, abandoned, Ser. No. 298,692, Oct. 18, 1972, abandoned, Ser. No. 245,608, April 19, 1972, Pat. No. 3,865,931, and Ser. No. 235,015, March 15, 1972, abandoned.

[52] U.S. Cl. 260/294.8 F; 260/294.8 G; 260/294.9; 260/295.5 C; 424/84; 424/263; 424/266
[51] Int. Cl.² .................................. C07D 213/75
[58] Field of Search ... 260/294.8 F, 294.8 G, 294.9, 260/295.5 C

[56] References Cited

UNITED STATES PATENTS

| | | | |
|---|---|---|---|
| 2,681,879 | 6/1954 | Gysin et al. | 424/84 |
| 3,284,461 | 11/1966 | Wilbert et al. | 260/295 CA |
| 3,428,642 | 2/1969 | Debay et al. | 260/295 CA |
| 3,584,000 | 6/1971 | Hobart et al. | 260/295.5 C |
| 3,676,457 | 7/1972 | Hubele et al. | 424/300 |

FOREIGN PATENTS OR APPLICATIONS

| | | | |
|---|---|---|---|
| 1,132,988 | 11/1968 | United Kingdom | 260/295 CA |

*Primary Examiner*—Alan L. Rotman

[57] ABSTRACT

Certain 3-pyridylmethyl N-(4'-substituted-phenyl)carbamates are useful as rodenticides, e.g., in baits or tracking powders. The 4'-substituent may be $-NO_2$, $-CN$, $-CF_3$, $-SO_2NH_2$, $-SR$, $-SOR$ or $-SO_2R$ where R is lower alkyl. Their salts can also be made and applied as rodenticides.

12 Claims, No Drawings

PYRIDYL PHENYL-CARBAMATE RODENTICIDES

CROSS-REFERENCE TO RELATED APPLICATIONS

This is a continuation-in-part of applications Ser. No. 428,463, filed Dec. 26, 1973 now abandoned; Ser. No. 298,692, filed Oct. 18, 1972, now abandoned; Ser. No. 245,608, filed Apr. 19, 1972; now U.S. Pat. No. 3,865,931 dated Feb. 11, 1975 and Ser. No. 235,015, filed Mar. 15, 1972 now abandoned.

BACKGROUND OF THE INVENTION

1. Field of the Invention

The present invention relates to rodenticides and more particularly to the use of compositions containing certain pyridyl phenyl carbamates or their acid salts or metal salt complexes for the control and extermination of pest rodents.

2. Description of the Prior Art

The common rat, *Rattus norvegicus*, is vicious and constantly poses a serious threat to the health and well being of man. Rats and mice are destructive animals and a serious nuisance, causing millions of dollars damage annually to farms, agronomic crops, homes, food processing plants and many other businesses. Rats bite at least 14,000 (possibly up to 60,000) people every year in the U.S.A., according to the U.S. Public Health Service, and are known carriers of over 35 contagious diseases including bubonic plague, trichinosis, typhus, rat bite fever, amoebic dysentery, tuberculosis, infectious jaundice and rabies. During the years from 1898 to 1923, almost 11 million deaths were caused by rat-borne plagues.

Use of rodenticides, fumigants, sprays and traps are the primary methods employed for the control of pest rodents. By "pest rodents" we refer not only to members of the order Rodentia but also to those of Lagomorpha, which cause health hazards or economic loss unless kept in check. Rodenticides may be used in the form of a tracking powder or a bait or may be applied as a spray on the rodent's natural foodstuffs. The rodenticides used as a bait are of two classes: single-dose and multi-dose. Multi-dose rodenticides are usually selected over single-dose rodenticides, as they have been safer in the past than the available single-dose rodenticides. The multi-dose rodenticides are anti-coagulants, including a number of different 4-hydroxy coumarin and 1,3-indandione compounds. These multi-dose rodenticides consumed in small daily amounts have a lethal effect on rats and mice after liver stores of viatmin K have been depleted. Anti-coagulants are less effective on mice than rats, as mice are considered to be nibblers and may not consume an adequate amount of treated bait to have a lethal effect. A single-dose rodenticide which would be relatively safe to the person handling the material and to non-target species of animals and yet effective on a variety of pest rodents is highly desirable.

SUMMARY OF THE INVENTION

Many compounds are toxic to rodents. However, very few of these compounds are anywhere near suitable for use as a rodenticide because it is necessary for the pest rodent to consume voluntarily a sufficient amount of the poison even though sufficient untreated food may also be available. In bait rodenticides, feed acceptance is the key to excellence, and in all rodenticides safety and efficacy are highly important.

The pyridyl phenyl-carbamates of the present invention are so highly toxic to a wide variety of pest rodents that a single dose is sufficient; yet they are relatively safe for use in the presence of other species which may inadvertently ingest limited quantities of the rodenticide. Furthermore, rats and other pest rodents willingly consume the compounds of the present invention in sufficiently lethal amounts when present in baits. Alternatively the compounds may be employed in compositions to be sprayed on natural foodstuffs. They may also be employed in tracking powder, especially for use against mice, which habitually clean their paws by licking.

The compounds of the present invention have the formula:

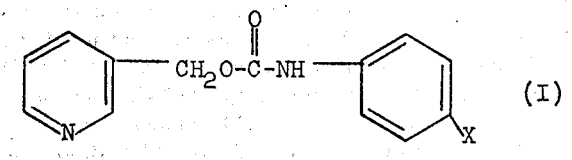

wherein X is selected from the group consisting of $-NO_2$, $-CN$, $-CF_3$, $-SR$, $-SOR$, $-SO_2R$, and $-SO_2NH_2$ where R is lower alkyl. By lower alkyl is meant alkyl groups, straight or branched, of 1 to 4 carbon atoms. It is to be noted that each of the para substituents on the phenyl ring is highly electron-withdrawing (i.e., its Hammet substituent constant $\sigma$ is greater than about +0.23) except for the $-SR$ group. This apparent anomaly is explained by the fact that $-SR$ substituents are commonly oxidized to $-SOR$ in vivo.

The compounds of the present invention in which the nitrogen of the pyridyl nucleus is in basic form as represented in Formula I, may be prepared by permitting equimolar amounts of a substituted phenylisocyanate and 3-pyridylcarbinol to react in the presence of an inert solvent, e.g., pyridine, an aromatic hydrocarbon or acetonitrile, in accordance with the following equation:

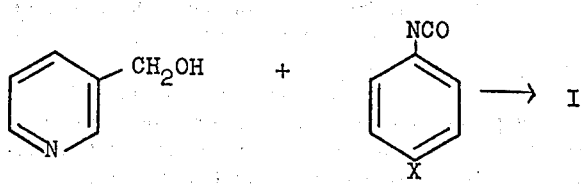

An example of this type of reaction is given in U.S. Pat. No. 3,284,461. 3-Pyridylcarbinol is a product of commerce. Certain of the phenyl isocyanates appear to be novel. They are made by the standard method of reaction of phosgene with the substituted aniline. They were identified by infra-red spectrum.

The following examples describe variations in the preparation of the basic compounds of the present invention.

EXAMPLE 1

Preparation of 3-pyridylmethyl N-(4'-nitrophenyl)carbamate a. Procedure 1 p-Nitrophenylisocyanate (0.1 mole) was added to a solution of 3-pyridylcarbinol (0.1 mole) in 300 ml. of benzene. An exothermic reaction took place and a yellow solid formed. The suspension was heated to reflux and then stirred for 2 hours. The suspension was then cooled and filtered, affording 27 g. of a crude product melting at 230°–231° C. (decomposed). This is a 99% yield of 3-pyridylmethyl N-(4'-nitrophenyl)-carbamate. The product was purified by recrystallization from 2-methoxyethanol (methyl Cellosolve).

b. Procedure 2

Commercial p-nitrophenyl isocyanate (100 g., Eastman Organic Chemicals) was purified by slurrying in 850 ml. of dry chlorobenzene for 15 minutes under anhydrous conditions and then vacuum filtering. The 26 g. of solid was discarded. To the filtrate, containing 74 g. (0.45 mole) of pure p-nitrophenylisocyanate in the 850 ml. chlorobenzene, was added dropwise 49.2 g. (0.45 mole) of 3-pyridylcarbinol over a period of 30 minutes. The temperature rose to 50° C. After about 1% of the 3-pyridylcarbinol had been added, a precipitate began to form, and after about 40% addition, the suspension showed considerable thickening. The suspension was stirred at room temperature overnight. Throughout the reaction, efficient stirring and anhydrous conditions were maintained. The solid product was recovered from the reaction mixture by filtration, washed thoroughly with cold acetone and dried in a vacuum oven, affording 123.2 g. of product, melting at 232°–234° C. (decomposed). This is a quantitative yield of 3-pyridylmethyl -N-(4'-nitrophenyl)-carbamate.

EXAMPLE 2

Preparation of 3-pyridylmethyl N-(4'-cyanophenyl)carbamate p-Tolylsulfonylisocyanate (39.4 g., 0.2 mole) in 100 ml. of ether was added dropwise to a solution of 4-aminobenzonitrile (23.6 g., 0.2 mole) in 300 ml. of ether. Reaction took place immediately with the formation of a white solid. After stirring for 1 hr. at room temperature, the suspension was filtered, and the white solid which was isolated was washed with ether and dried. The sulfonylurea weighed 59 g. and melted at 185° – 195°C.

The sulfonylurea was decomposed in vacuo at 1 mm. Hg using a shortpath heated tube. Since this apparatus did not have a ground glass temmperature joint, it was not possible to record the distillation temmperature. There was obtained 14 g. of 4-cyanophenylisocyanate.

4-Cyanophenylisocyanate (13.5 g., 0.1 mole) was dissolved in dry acetonitrile (50 ml.) and added to a solution of 3-pyridyl-carbinol (10.9 g., 0.1 mole) in dry acetonitrile (200 ml.). Reaction appeared complete in 5 min., but the suspension was stirred for an additional hour and then filtered. After washing with benzene and drying, the crude product amounted to 23.4 g.; melting point 175° – 182°C.

Chromatography over alumina using acetone as the eluant afforded 18 g. of product melting at 205° – 207°C. This is a 71% yield of 3-pyridylmethyl N-(4'-cyanophenyl)-carbamate. The product was recrystallized from 95% ethanol to afford a white solid; melting point 205° – 207°C.

EXAMPLE 3

Preparation of 3-pyridylmethyl N-(4'-trifluoromethylphenyl)-carbamate

To a solution of 2.5 g. (0.023 mole) of 3-pyridylcarbinol in 50 ml. of benzene containing 0.1 g. of Dabco catalyst (1,4-diazabicyclo [2,2,2] octane) was added, dropwise, a solution of 43 g. (0.023 mole) of p-trifluoromethyl-phenyl isocyanate in 50 ml. of benzene. A temperature rise from 23° to 35° was noted during the addition, and a white precipitate formed. After stirring for 1 hr., the mixture was filtered, and the solid product was air-dried. There was obtained 6.3 g. (93% of theory) of product; melting point 173° – 175° C. (decomposed). This is a 93% yield of 3-pyridylmethyl N-(4'-trifluoromethylphenyl)-carbamate.

EXAMPLE 4

Preparation of 3-pyridylmethyl N-(4'-methylthiophenyl)-carbamate

To a solution of 4.4 g. (0.04 mole) of 3-pyridylcarbinol in 50 ml. of benzene containing 0.1 g. of Dabco catalyst was added, dropwise, a solution of 6.6 g. (0.04 mole) of p-methylthiophenyl isocyanate (New Haven Chemicals) in 50 ml. of benzene. During the addition a white solid separated and the temperature rose from 23°C. to 34°C. The mixture was stirred at ambient temperature for 16 hrs. and the product was filtered off. After oven-drying in vacuo there was obtained 10.4 g. melting at 133° –135°C. This is a 95% yield of 3-pyridylmethyl N-(4'-methylthiophenyl)-carbamate.

EXAMPLE 8

Preparation of 3-pyridylmethyl N-(4'-methylsulfinylphenyl)-carbamate

Quinoline-bromine complex was prepared by adding 3.2 g. (0.02 mole) of bromine in 50 ml. of $CCl_4$ to a solution of 2.6 g. (0.02 mole) of quinoline in 50 ml. of $CCl_4$. A yellow solid separated which was filtered off and air-dried. The yield was 3.5 g. (60%). To a solution of 2.7 g. (0.01 mole) of 3-pyridylmethyl N-(4'-methylthiophenyl)carbamate in 100 ml. of 70% aqueous acetic acid was added, portionwise, 2.7 g. (0.01 mole) of the quinoline-bromine complex. The mixture was stirred at ambient temperature for 15 min. and poured into 100 ml. of water. A negligible amount of solid formed and was removed by filtration. The filtrate was made alkaline with 25% aqueous NaOH, and a white precipitate formed which was filtered off and recrystallized from aqueous ethanol. There was obtained 0.5 g. of recrystallized product, melting at 118° – 121°C., which proved to be a mixture of two components by thin layer chromatography. The filtrate was concentrated to near-dryness, and yielded after oven drying in vacuo 1 g. of a white solid melting at 139° – 143° C. This was a 34% yield of 3-pyridylmethyl N-(4'-methylsulfinylphenyl)-carbamate.

EXAMPLE 9

Preparation of 3-pyridylmethyl N-(4'-methylsulfonylphenyl)-carbamate

To an ice-cold slurry of 6.2 g. (0.036 mole) of m-chloroperbenzoic acid in 100 ml. of benzene was added, portionwise, 4.1 g. (0.015 mole) of 3-pyridylmethyl N-(4'-methylthiophenyl)carbamate, keeping the temperature below 10°C. When the addition was complete, the mixture was stirred at ambient temperature for 16 hrs. Removal of the acidic by-product was accomplished by adding 100 ml. of saturated sodium carbonate solution, stirring for 1 hr., and filtering. The solid product was oven-dried in vacuo to give 3.3 g. of crude product melting at 169° – 173°C. (decomposed). This was a 72% yield of 3-pyridylmethyl N-(4'-methylsulfonylphenyl)carbamate. Recrystallization from 95% ethanol raised the melting poing to 175°–178°C. (decomposed).

EXAMPLE 13

Preparation of 3-pyridylmethyl N-(4'-sulfamylphenyl)-carbamate

To a solution of 3.25 g. (0.05 mole) sodium azide in 15 ml. water and 15 ml. acetone was added dropwise a solution of 8.25 g. (0.0375 ml.) p-sulfamyl benzoyl chloride in 75 ml. of acetone. The addition took place over a 15 minute period with the temperature being maintained at 0°C. The mixture was stirred at 0° for one hour, after which there was added 150 ml. of water and 100 ml. of toluene. The suspension formed was vacuum-filtered, and the first crop of p-sulfamyl carbonyl azide was air-dried for 15 minutes (melting point 134°C. violent decomp.). The p-sulfamyl carbonyl azide was dissolved in 200 ml. of anhydrous ethylene glycol dimethyl ether, hereinafter "glyme," dried over magnesium sulfate, and reacted in the following manner:

To a solution of p-sulfamyl carbonyl azide in 200 ml. of anhydrous glyme was added dropwise 7.25 g. (0.0665 mole) of 3-pyridylcarbinol. The resultant solution was refluxed and stirred for 3 hours and was let stand for 18 hours. The suspension formed was vacuum-filtered to remove 0.5 g. of bis-p-sulfamylphenylurea. The filtrate was poured into an excess of ether, and the suspension formed was vacuum-filtered to afford 2 g. (17.3% yield) of product melting at 174°C. (decomposed). This is a 17.3% yield of 3-pyridylmethyl N-(4'-sulfamylphenyl) carbamate.

The following Tables I and II respectively give physical constants for certain intermediates and the novel compounds of this invention:

TABLE I

| Used In Example | X = | 4-XC$_6$H$_4$NCO Intermediates Melting point (°C) or Boiling point °C/pressure mm. |
|---|---|---|
| 1 | NO$_2$ | a commercial product |
| 2 | CN | not isolated |
| 3 | CF$_3$ | German patent no. 1,138,391 |
| 4 | —SCH$_3$ | a commercial product |

TABLE I-continued

| Used In Example | X = | 4-XC$_6$H$_4$NCO Intermediates Melting point (°C) or Boiling point °C/pressure mm. |
|---|---|---|
| 5 | —SC$_2$H$_5$ | 67–72/0.25 mm. |
| 6 | —SC$_3$H$_7$-n | 90–95/0.4 mm. |
| 7 | —SC$_4$H$_9$-n | 105–109/0.35 mm. |
| 10 | —SO$_2$C$_3$H$_7$-n | oil |
| 11 | —SO$_2$C$_3$H$_7$-iso | 48–55 |
| 12 | —SO$_2$C$_4$H$_9$-n | oil |
| 13 | —SO$_2$NH$_2$ | J. Org. Chem. 30, 1260(1965) |

TABLE II

3-PYRIDYL-CH$_2$OC(O)NHC$_6$H$_4$X-4 COMPOUNDS

| Example | X= | Melting Point (°C.) | Empirical Formula | Analysis * C | H | N |
|---|---|---|---|---|---|---|
| 1 | NO$_2$ | 232 – 234 (dec.) | C$_{13}$H$_{11}$N$_3$O$_4$ | 57.3 (57.2) | 4.0 (4.1) | 15.5 (15.4) |
| 2 | CN | 205 – 207 | C$_{14}$H$_{11}$N$_3$O$_2$ | 66.4 (66.4) | 4.1 (4.4) | 16.8 (16.6) |
| 3 | CF$_3$ | 173 – 175 (dec.) | C$_{14}$H$_{11}$F$_3$N$_2$O$_2$ | 56.7 (56.8) | 3.7 (3.7) | 9.4 (9.5) |
| 4 | —SCH$_3$ | 133 – 135 | C$_{14}$H$_{14}$N$_2$O$_2$S | 61.3 (61.3) | 5.0 (5.1) | 10.2 (10.2) |
| 5 | —SC$_2$H$_5$ | 116 – 119 | C$_{15}$H$_{16}$N$_2$O$_2$S | 62.5 (62.3) | 5.6 (5.5) | 9.4 (9.7) |
| 6 | —SC$_3$H$_7$-n | 124 – 126 | C$_{16}$H$_{18}$N$_2$O$_2$S | 63.3 (63.6) | 6.1 (6.0) | 9.1 (9.3) |
| 7 | —SC$_4$H$_9$-n | 115 – 117 | C$_{17}$H$_{20}$N$_2$O$_2$S | 64.5 (64.5) | 6.4 (6.4) | 8.8 (8.9) |
| 8 | —SOCH$_3$ | 139 – 143 | C$_{14}$H$_{14}$N$_2$O$_3$S | 58.0 (58.0) | 4.9 (4.9) | 9.5 (9.7) |
| 9 | —SO$_2$CH$_3$ | 175 – 178(dec.) | C$_{14}$H$_{14}$N$_2$O$_4$S | 55.1 (54.9) | 4.6 (4.6) | 9.1 (9.2) |
| 10 | —SO$_2$C$_3$H$_7$-n | 164 – 166 | C$_{16}$H$_{18}$N$_2$O$_4$S | 57.4 (57.5) | 5.5 (5.4) | 8.2 (8.4) |
| 11 | —SO$_2$C$_3$H$_7$-iso | 122 – 125 | C$_{16}$H$_{18}$N$_2$O$_4$S | 57.3 (57.5) | 5.3 (5.4) | 8.1 (8.4) |
| 12 | —SO$_2$C$_4$H$_9$-n | 156 – 160 | C$_{17}$H$_{20}$N$_2$O$_4$S | 58.0 (58.6) | 5.6 (5.8) | 7.9 (8.0) |
| 13 | —SO$_2$NH$_2$ | 174 (dec.) | C$_{13}$H$_{13}$N$_3$O$_4$S | 49.6 (50.8) | 4.5 (4.3) | 13.8 (13.7) |

* The number in parenthesis represents the theoretical value as calculated from the empirical formula The compounds of the invention may also be made and/or used in salt form. Generally, to make an acid salt, the basic form of the compound represented in Formula I above is dissolved in a suitable solvent such as acetonitrile, monomethyl ether of ethylene glycol, dimethyl formamide, dimethyl acetamide, acetone, or other suitable solvent; and the acid is introduced into the solution of the base form of compound either as a gas, a liquid, or a solid. Depending on the particular compound, acid, and solvent medium, the salt formed may precipitate or it may remain in solution. In the latter case, it is only necessary to add a suitable non-solvent for the salt to precipitate it out. For example, the non-solvent may be ether in some instances, or it may be an aliphatic or aromatic hydrocarbon such as hexane, benzene, toluene, or xylene in other instances. When the salt has been precipitated, it is merely necessary to filter it, wash the precipitate, and dry the salt. The salts may be those of an inorganic or an organic acid. Preferred acid salts are those formed especially strong acids, especiailly acetic, hydrobromic, hydrochloric, hydrofluoric, nitric, phosphoric, sulfuric, chloroacetic, oxalic, maleic, succinic and p-toluenesulfonic acids. Frequently, if not always, the salt form dissociates and liberates the base form of the compound and the free acid either in the environment where applied for rodenticidal purposes or in the rodent's system during or after ingestion.

Illustrative salt preparations that may be used are:

EXAMPLE 1A

Preparation of hydrobromide of 3-pyridylmethyl N-(4'-nitrophenyl)carbamate

Gaseous HBr is passed into a solution of 5 g. of 3-pyridylmethyl N-(4'-nitrophenyl)carbamate in 75 ml. of the monomethyl ether of ethylene glycol. Ether is added to give a precipitate which, after washing with ether, amounted to 4.5 g. of white solid. This, on analysis contains 44.45% C, 3.48% H, 11.55% N and 21.45%

Br; calculated for $C_{13}H_{11}N_3O_4 \cdot HBr$ is 44.09% C, 3.42% H, 11.86% N and 22.56% Br. The product is a 69% yield of 3-pyridylmethyl N-(4'-nitrophenyl)carbamate hydrobromide.

EXAMPLE 1B

To a filtered, warm solution of 2.7 g. (0.01 mole) of 3-pyridylmethyl N-(4'-nitrophenyl)carbamate in 400 ml. of the monomethyl ether of ethyleneglycol (glyme) is added a solution of 1.3 g. (0.01 mole) of anhydrous $CuCl_2$ in 15 ml. of glyme. Cooling gives a precipitate which is isolated by filtration to give 2.9 g. of a blue solid melting at 270°–272° C. This is found by analysis to contain 45.19% C, 3.5% H, 12.24% N, 9.28% Cu and 10.54% Cl; calculated for $C_{13}H_{11}N_3O_4 \cdot \frac{1}{2} CuCl_2$ is 45.82% C, 3.25% H, 12.34% N, 9.33% Cu and 10.41% Cl. The product is an 85% yield of 3-pyridylmethyl N-(4'-nitrophenyl) carbamate-cupric chloride complex.

EXAMPLE 1C

When cadmium chloride is substituted for cupric chloride in the above preparation (Ex. 1B), there is obtained 3.3 g. of white solid melting at 270° C. with decomposition. This is found on analysis to contain 37.36% C, 2.70% H, 10.22% N, 12.03% Cl and 19.23% Cd; calculated for $C_{13}H_{11}N_3O_4 \cdot \frac{1}{2} CdCl_2$ is 42.79% C, 3.04% N, 11.52% N, 9.44% Cl and 15.40% Cd. The product is considered to be a 73% weight yield of 3-pyridylmethyl N-(4'-nitrophenyl) carbamate-cadmium chloride complex.

EXAMPLE 1D

When zinc chloride is substituted for the cupric chloride in the above described preparation (Ex. 1B), there is obtained 2.3 g. of a white solid melting at 185°–189° C. with decomposition. This is found on analysis to contain 45.88% C, 3.66% H, 11.63% N, 10.39% Cl and 10.30% Zn; calculated for $C_{13}H_{11}N_3O_4 \cdot \frac{1}{2} ZnCl_2$ is 45.87% C, 3.25% H, 12.35% N, 10.41% Cl and 9.60% Zn.

EXAMPLE 2A a. In a manner similar to that of Ex. 1A, the following salts of 3-pyridylmethyl N-(4-cyanophenyl) carbamate (Ex. 2) are prepared:

1. The hydrobromide
2. The hydrochloride, and
3. The hydrofluoride b. The following metal salt complexes of the carbamate of Ex. 2 are prepared by procedures analogous to those of Exs. 1B, 1C, and 1D:

1. $ZnCl_2$
2. $ZnBr_2$
3. $CuCl_2$
4. $MnCl_2$
5. $Cu(NO_3)_2$
6. $NiCl_2$ c. The oxalate is prepared by a procedure analogous to that of Ex. 4A a) hereinafter.

EXAMPLE 3A a. The following salts may be made from the product of Ex. 3 in a way analogous to the procedure of Ex. 1A above:

1. The hydrobromide
2. The hydrochloride b. The oxalate may be prepared by the procedure of Ex. 4A a) below.

EXAMPLE 4A a. To a solution of 3-pyridylmethyl N-(4'-(methylthio)phenyl) carbamate (5 g., 0.0183 mole) in 75 ml. of ethylene glycol monomethyl ether there is added oxalic acid dihydrate (2.3 g., 0.0183 mole) in 15 ml. of ethylene glycol monomethyl ether. The reaction mixture is allowed to stand at room temperature over the weekend. The precipitate formed is washed with ethylene glycol monomethyl ether and dried to give 3.3 g. of a solid melting at 154°–156° C. This is a 50% yield of the oxalic acid salt of 3-pyridylmethyl N-(4'-(methylthio)-phenyl)carbamate. This, on analysis, contains 52.9% C, 4.5% H and 7.6% N. Theory calls for 52.7% C, 4.4% H, and 7.7% N.

b. The following salts may also be prepared from the compound of Ex. 4:

1. The hydrobromide
2. The hydrochloride
3. The maleate
4. The $ZnCl_2$ complex salt.

Similar salts can be prepared from the products of Ex. 5, 6, and 7.

EXAMPLE 8A

The oxalate and phosphate salts of the compound of Ex. 8 can be made by a procedure analogous to that of Ex. 4A above.

EXAMPLE 9A

The following salts may be made from the compound obtained in Ex. 9:

1. The hydrochloride
2. The nitrate
3. The chloroacetate
4. The p-toluenesulfonate Similarly, the hydrochlorides may be made from Ex. 10, 11, and 12.

EXAMPLE 13A

The product of Ex. 13 may be formed into the following salts in a manner generally described hereinabove:

1. The acetate
2. The hydrochloride
3. The oxalate

In general, the salts tested have been found to be as effective as the base form of the compounds in rodentical action.

FORMULATION FOR USE

The compounds of the present invention or a salt thereof may be formulated into rodenticide compositions such as baits, tracking powders, and sprays. A bait comprises an edible carrier and the toxicant, optionally with a preservative to prevent insect infestation, mold growth or rancidity. The edible carrier may be a semi-moist material such as canned cat or dog food or garbage such as apples, eggs, baacon, etc., but it is generally preferred to use a dry edible carrier as this remains acceptable for longer periods. The dry carrier may be a combination of natural food products such as whole ground corn, steel cut oats, sugar, molasses, rice, vegetable oil, salt, dehydrated fruit, fish meal, tankage or wheat. When necessary to use in damp locations, the matrix may be a water repellent material such as paraffin wax or an acrylic polymer.

The compounds of the present invention may be incorporated as toxicant in bait formulations, either alone or in combination with other toxicants. When used as the sole toxicant in baits, the compounds of the present invention may be used in any rodenticidally effective concentration.

Depending on the susceptibility of the rodents to the toxicant and the amount of formulated bait generally consumed, concentrations as low as 0.1 percent, and especially when intended for mice, even lower than 0.05 percent may be employed. A typical bait may contain between about 0.5 percent and 1.5 percent of the toxicant by weight. We have found to our surprise that there is no upper limit to the amount of compound which may be present in a bait. Rats, mice and other rodents accept the compounds of the present invention so well that even when offered free choice between untreated basal ration and a bait consisting entirely of one of the present compounds, they ingest rodenticidally sufficient quantities of the compound. Example 14 describes the formulation of a suitable bait, although wide variations in formulation for different conditions of use are of course expected.

Tracking powders, which are particularly effective against mice, may be either a compound of the present invention in finely powdered form or a mixture of the compound with a powdered carrier, e.g., talc, sugar, milk powder, Indian corn meal, fish meal, cornstarch, flour, and bentonite, or the like, or any combination thereof which tends to induce the animals contaminated with the preparation to lick themselves more thoroughly. In tracking powders, the compounds of the present invention may be incorporated in amounts from 100 down to 0.75 percent by weight, or somewhat less with proper formulation. Preferably, the compound(s) is present in a range of about 0.75 to about 50 percent by weight, based on the weight of the total composition. Example 15 describes the preparation of a suitable tracking powder.

EXAMPLE 14

Bait Formulation

Each of the compounds of Examples 1–13 was blended with the basal ration in a Waring laboratory blender to form 50 grams of a homogeneous premix. The amount of compound utilized was determined by the percentage of active material desired in the feed. The formula for the basal ration is shown below, all percentages being by weight:

| | |
|---|---|
| Crude ground corn | 65% |
| Steel cut oats | 25% |
| Powdered sugar | 5% |
| Corn oil | 5% |

The 50 grams of premix containing the toxicant were then mixed with an additional 450 grams of basal ration. These components were mixed in a Little Ford Lodige mixer for three minutes.

EXAMPLE 15

The active compound is finely pulverized by mortar and pestle to form a 100 percent active tracking powder. To form a 5 percent active material, it may be mixed with 10X confectioner's sugar in a 1 to 19 ratio and at other ratios for other levels of active compound.

The compounds are preliminarly evaluated for their ability to kill albino rats (*Rattus norvegicus*) by oral administration to two rats at a dosage of 50 mg./kg. The effect on the rats is observed at intervals up to 14 days later. If at least one of the rats dies within this period, the compound is then subjected to secondary tests described hereinafter.

All of the compounds of Formula I wherein R is $-NO_2$, $-CN$, $-CF_3$, $-SCH_3$, $-SC_2H_5$, $-SC_3H_7$-n, $-SC_3H_7$-iso, $-SC_4H_9$-n, $-SC_4H_9$-iso, $-SC_4H_9$-sec, $-SOCH_3$, $-SO_2CH_3$, $-SO_2C_3H_7$-n, $-SO_2C_3H_7$-iso, $-SO_2C_4H_9$-n, $-SO_2NH_2$, pass the preliminary test, most of them killing two out of the two test rats. The salts thereof have similar effectiveness, again killing two out of the two test rats in most instances.

One of the most significant secondary tests is a standard one known as the paired preference test. In this test, the rodents are given a free choice between the treated and untreated bait. Such a test most nearly approximates practical use conditions.

Paired Preference Tests

When caged individually, they were provided with dual feed cups and separate water devices. When caged in a communal tank, they were offered a multiplicity of feed cups and water devices. The basal ration was offered in excess of daily feed requirements in each of two feeders: one treated with the test compound and one without. For each test, equal numbers of each sex were used.

The gross weight of each feed container and its feed were determined daily and returned to the starting weight by addition of complete replacement of the given diet. The position of the bait and the laboratory diet cups in the cage were reversed every 24 hours to counter any feeding position habit of the rat. The test rodents had free choice between treated and untreated feed. Mortalities were recorded daily.

To meet the criteria for a single-dose product, a rodenticide in this initial test must kill 75 percent of the rats within 8 days, where the poison bait is available for the first 72 hours of this period.

The results of representative paired preference tests on individually caged commercial albino rats with several compounds of Formula I (wherein the substituent X in the para position of the phenyl group is as indicated in the table) are given in Table III.

TABLE III

Paired Preference Test of
3-Pyridylmethyl N-(4'-X-phenyl)carbamate

| Example | X | Compound in Basal Ration Parts/Million | Rats Killed (in 8 days)/ Rats in Test |
|---|---|---|---|
| 1 | $-NO_2$ | 50,000 | 2/2 |
|  |  | 5,000 | 3/4 |
|  |  | 2,500 | 4/4 |
|  |  | 1,250 | 3/4 |
|  |  | 1,000 | 0/2 |
|  |  | 625 | 4/4 |
|  |  | 312 | 0/4 |
| 1D | $-NO_2(ZnCl_2$ complex) | 10,000 | 2/2 |
| 2 | $-CN$ | 3,000 | 4/4 |
| 3 | $-CF_3$ | 3,000 | 4/4 |
| 4 | $-SCH_3$ | 100,000 | 4/4 |
|  |  | 50,000 | 2/2 |
|  |  | 10,000 | 4/4 |
|  |  | 3,000 | 4/4 |
|  |  | 1,000 | 4/4 |
|  |  | 500 | 4/4 |
|  |  | 300 | 4/4 |
|  |  | 100 | 2/4 |
|  |  | 50 | 0/4 |
| 7 | $-SC_4H_9-n$ | 3,000 | 3/4 |
| 8 | $-SOCH_3$ | 3,000 | 4/4 |
| 9 | $-SO_2CH_3$ | 50,000 | 2/2 |
|  |  | 3,000 | 4/4 |
|  |  | 1,000 | 2/2 |
| 10 | $-SO_2C_3H_7-n$ | 3,000 | 4/4 |
| 13 | $-SO_2 NH_2$ | 50,000 | 2/2 |
|  |  | 3,000 | 3/4 |
|  |  | 1,000 | 0/2 |

The results of representative paired preference tests with Examples 1 and 4 on individually caged Norway rats (*Rattus norvegicus*) are shown in Table IV.

TABLE IV

Paired Preference Test
Using Individually Caged Norway Rats

| | Compound in Basal Ration (Parts per Million) | Rats Killed (in 8 days) Per Rats in Test |
|---|---|---|
| a) | Example 1 | |
|  | 100,000 | 4/4 |
|  | 50,000 | 4/4 |
|  | 20,000 | 4/4 |
|  | 15,000 | 4/4 |
|  | 10,000 | 4/4 |
|  | 5,000 | 4/4 |
|  | 3,000 | 19/20 |
|  | 2,000 | 17/20 |
|  | 2,000 | 4/4 |
|  | 1,000 | 4/4 |
|  | 500 | 0/4 |
| b) | Example 4 | |
|  | 100,000 | 4/4 |
|  | 10,000 | 4/4 |
|  | 5,000 | 4/4 |
|  | 2,500 | 19/20 |
|  | 2,500 | 4/4 |
|  | 1,250 | 4/4 |
|  | 625 | 3/4 |

The results of paired preference tests of 3-pyridylmethyl N-(4'-substituted-phenyl)carbamate using 20 rats housed in a communal "tank" are shown in Table V. This is a stringent test, since the more resistant animals may learn to avoid the bait by observing the toxic effects on their cage-mates. At the 5,000 p.p.m. level, the requirement of 90 percent mortality was satisfied.

TABLE V

Paired Preference Test
Using Norway Rats in a Communal Tank

| | Compound in Basal Ration (Parts per Million) | Rats Killed (in 8 days) Per Rats in Test |
|---|---|---|
| a) | Example 1 | |
|  | 10,000 | 18/20 |
|  | 5,000 | 18/20 |
|  | 3,000 | 15/20 |
| b) | Example 4 | |
|  | 2,500 | 20/20 |

The paired preference test was conducted on individually caged roof rats (*Rattus rattus*) with Examples 1 and 4. The results are given in Table VI.

TABLE VI

Paired Preference Test
Using Individually Caged Roof Rats

| | Compound in Basal Ration (Parts per Million) | Rats Killed (in 8 days) Per Rats in Test |
|---|---|---|
| a) | Example 1 | |
|  | 50,000 | 0/2 |
| b) | Example 4 | |
|  | 100,000 | 4/4 |
|  | 10,000 | 4/4 |
|  | 5,000 | 3/4 |
|  | 2,500 | 4/4 |
|  | 2,500 | 19/20 |
|  | 1,250 | 3/4 |
|  | 625 | 2/4 |
|  | 312 | 0/4 |

The results of the paired preference test with Example 4 at 2500 ppm. using 20 roof rats in a communal tank gave 18 rats killed out of 20 within 8 days.

The results of representative paired preference tests with Examples 1 and 4 on individually caged feral (house) mice (*Mus musculus*) which were trapped on local farms are given in Table VII.

TABLE VII

Paired Preference Test
Using Individually Caged Feral Mice

| | Compound in Basal Ration (Parts Per Million) | Mice Killed (in 8 days) Per Mice in Test |
|---|---|---|
| a) | Example 1 | |
|  | 100,000 | 4/4 |
|  | 50,000 | 4/4 |
|  | 10,000 | 4/4 |
|  | 10,000 | 15/20 |
|  | 5,000 | 19/20 |
|  | 4,000 | 3/4 |
|  | 3,000 | 3/4 |
|  | 2,000 | 4/4 |
|  | 1,000 | 3/4 |
|  | 500 | 4/4 |
| b) | Example 4 | |
|  | 100,000 | 4/4 |
|  | 10,000 | 4/4 |
|  | 5,000 | 4/4 |
|  | 2,500 | 4/4 |
|  | 1,250 | 3/4 |
|  | 625 | 2/4 |
|  | 312 | 4/4 |
|  | 156 | 4/4 |
|  | 75 | 0/4 |

The results of the paired preference test with Example 1 at 10,000 ppm using 20 feral mice housed in a communal tank gave 19 mice killed out of 20 within 8 days.

The paired preference test was run on individually caged deer mice (*Peromyscus spp.*) trapped on local farms with the compounds of Examples 1 and 4. The results are given in Table VIII.

TABLE VIII

Paired Preference Test
Using Individually Deer Mice

| Compound in Basal Ration (Parts per Million) | Deer Mice Killed (in 8 days) Per Mice in Test |
|---|---|
| a) Example 1 | |
| 10,000 | 4/4 |
| 5,000 | 4/4 |
| 2,500 | 4/4 |
| 2,500 | 19/20 |
| 1,250 | 3/4 |
| 625 | 1/4 |
| 312 | 0/4 |
| b) Example 4 | |
| 100,000 | 4/4 |
| 10,000 | 4/4 |
| 5,000 | 4/4 |
| 2,500 | 4/4 |
| 2,500 | 19/20 |
| 1,250 | 3/4 |
| 625 | 1/4 |
| 312 | 0/4 |

The paired preference test was conducted on individually caged ground moles (*Microtus spp.*) trapped on local farms with the compound of Example 4. The results are given in Table IX.

TABLE IX

Paired Preference Test
Using Individually caged Microtus

| Compound in Basal Ration (Parts Per Million) | Microtus Killed (in 8 days) Per Microtus in Test |
|---|---|
| 2,500 | 2/2 |
| 2,500 | 18/20 |
| 1,250 | 2/2 |

Another secondary testing procedure is known as the tracking test. In this test the rodents are permitted to walk over areas on which the tracking powder has been placed. One such procedure follows:

MOUSE TRACKING TEST

Feral mice (*Mus musculus*) were each placed in a double cage system for these evaluations. The two cages of each system were connected by a tunnel. The tracking powder or toxicant was placed in the connecting tunnel and on entry pans. Feed and water were provided ad libitum, the water in one compartment of the cage and the feed in the other. An effective single-dose compound will kill 90 percent of the mice within 8 days, of which they are exposed during the first 72 hours.

The results of representative mouse tracking tests with the compounds of Examples 1 and 4 are shown in Table X.

TABLE X

Tracking Test Using Feral Mice

| Compound in Tracking Powder | Mice Killed (in 8 days) Per Mice in Test |
|---|---|
| a) Example 1 | |
| 100% | 4/4 |
| 50% | 4/4 |
| 10% | 4/4 |
| 5% | 19/20 |
| 3% | 4/4 |
| 1% | 4/4 |
| 0.75% | 3/4 |
| 0.50% | 2/4 |
| 0.25% | 0/4 |
| b) Example 4 | |
| 10% | 4/4 |
| 5% | 4/4 |
| 2.5% | 4/4 |
| 1.25% | 4/4 |
| .625 | 4/4 |
| .312 | 4/4 |
| .156 | 1/4 |

SPECIFICITY

For general use, 3-pyridylmethyl N-(4'-nitrophenyl)-carbamate is preferred as it has been found even less toxic to animals other than rodents which might inadvertently ingest the rodenticide than the other compounds of the present invention. Since the use of a rodenticide on a poultry farm might lead to chickens feeding on the bait, it is significant that this compound has been found to be safe with chickens. For example, one sample of 3-pyridylmethyl N-(4'-nitrophenyl)carbamate at 15,000 p.p.m. in the basal ration described above was offered to eight 14-day-old White Leghorn cockerels. On the basis of average feed consumption of a 48-hour period, the compound was found to have been taken at the rate of 800 mg/kg. After initial symptoms of toxicity lasting for less than two weeks, all of the chicks survived with no gross pathology. Apparently the ration containing the compound was unpalatable to the chicks, since the feed consumption of this group during the first week was depressed compared to a control group fed the untreated basal ration.

A similar group of chicks was dosed with the compound via capsule at 4000 mg/kg.; they exhibited stronger symptoms of toxicity than the former group but all recovered within two weeks with no gross pathology.

It is also desirable that a rodenticide be safe in the presence of wild birds, which might inadvertently ingest the bait. Three sets of two adult, male pigeons were dosed via capsule with the aforesaid compound, respectively at 500, 2000, and 4000 mg./kg. All of the pigeons survived, with no gross pathology.

Mammals other than the target species should preferably be unaffected by a rodenticide. When the aforesaid carbamate compound was administered in methylcellulose suspension by gastric intubation at levels of up to 1,000 mg/kg., mongrel dogs showed no significant grossly observable symptoms and no methomeglobin formation in the blood.

We claim:
1. A compund having the formula:

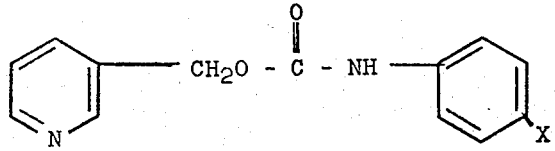

wherein X is selected from the group consisting of —NO$_2$, —CN, —CF$_3$, —SR, —SOR, —SO$_2$R, and —SO$_2$NH$_2$ wherein R is lower alkyl.

2. A compound of claim 1 wherein X is —$NO_2$.
3. A compound of claim 1 wherein X is —CN.
4. A compound of claim 1 wherein X is —$CF_3$.
5. A compound of claim 1 wherein X is —SR, R being lower alkyl.
6. A compound of claim 6 wherein X is —$SCH_3$.
7. A compound of claim 1 wherein X is —$SO_nR$ wherein $n$ may be 1 or 2 and R is lower alkyl.
8. A compound of claim 7 wherein R is methyl and $n$ is 1.
9. A compound of claim 7 wherein R is methyl and $n$ is 2.
10. A compound of claim 7 wherein R is ethyl and $n$ is 1.
11. A compound of claim 1 wherein X is —$SO_2NH_2$.
12. A compound of claim 1 in the form of a strong acid salt thereof.

* * * * *

UNITED STATES PATENT OFFICE
CERTIFICATE OF CORRECTION

Patent No. 3,931,202    Dated January 6, 1976

Inventor(s) J.E. WARE, E.E. KILBOURN and D.L. PEARDON

It is certified that error appears in the above-identified patent and that said Letters Patent are hereby corrected as shown below:

In claim 6, change "claim 6" to read --claim 5--.

Signed and Sealed this sixth Day of April 1976

[SEAL]

Attest:

RUTH C. MASON
Attesting Officer

C. MARSHALL DANN
Commissioner of Patents and Trademarks